US00PP24576P2

(12) United States Plant Patent
de Jong

(10) Patent No.: US PP24,576 P2
(45) Date of Patent: Jun. 24, 2014

(54) ***HYPERICUM* PLANT NAMED 'KOLMAPUKI'**

(50) Latin Name: *Hypericum×inodorum*
Varietal Denomination: Kolmapuki

(71) Applicant: Jan de Jong, Heelsum (NL)

(72) Inventor: Jan de Jong, Heelsum (NL)

(73) Assignee: Kolster Holding, B.V., Boskoop (NL)

( * ) Notice: Subject to any disclaimer, the term of this patent is extended or adjusted under 35 U.S.C. 154(b) by 8 days.

(21) Appl. No.: 13/694,020

(22) Filed: Oct. 20, 2012

(51) Int. Cl.
*A01H 5/00* (2006.01)

(52) U.S. Cl.
USPC ..... Plt./442

(58) Field of Classification Search
USPC ..... Plt./442, 263.1, 226
See application file for complete search history.

*Primary Examiner* — Kent L Bell
(74) *Attorney, Agent, or Firm* — C. A. Whealy

(57) ABSTRACT

A new and distinct cultivar of *Hypericum* plant named 'Kolmapuki', characterized by its upright and outwardly spreading plant habit; moderately vigorous growth habit; relatively small dark green-colored leaves; uniform and freely flowering habit; uniform and high density of fruits; orange-colored fruits; and resistance to *Puccinia* rust.

3 Drawing Sheets

Botanical designation: *Hypericum×inodorum.*
Cultivar denomination: 'KOLMAPUKI'.

BACKGROUND OF THE INVENTION

The present invention relates to a new and distinct cultivar of *Hypericum* plant, botanically known as *Hypericum×inodorum* and hereinafter referred to by the name 'Kolmapuki'.

The new *Hypericum* plant is a product of a planned breeding program conducted by the Inventor in Heelsum, The Netherlands. The objective of the breeding program is to create new pot-type *Hypericum* plants with strong stems, healthy foliage, numerous large fruits with unique coloration and resistance to *Puccinia* rust.

The new *Hypericum* plant originated from a cross-pollination conducted by the Inventor in 2007 in Heelsum, The Netherlands of a proprietary selection of *Hypericum×inodorum* identified as code number 261-01, not patented, as the female, or seed parent with a proprietary selection of *Hypericum×inodorum* identified as code number 229-04, not patented, as the male, or pollen, parent. The new *Hypericum* plant was discovered and selected by the Inventor as a single flowering plant from within the progeny of the stated cross-pollination in a controlled greenhouse environment in Heelsum, The Netherlands in 2008.

Asexual reproduction of the new *Hypericum* plant by vegetative cuttings in Boskoop, The Netherlands since 2008 has shown that the unique features of this new *Hypericum* plant are stable and reproduced true to type in successive generations.

SUMMARY OF THE INVENTION

Plants of the new *Hypericum* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Kolmapuki'.

These characteristics in combination distinguish 'Kolmapuki' as a new and distinct *Hypericum* plant:

1. Upright and outwardly spreading plant habit.
2. Moderately vigorous growth habit.
3. Relatively small dark green-colored leaves.
4. Uniform and freely flowering habit; uniform and high density of fruits.
5. Orange-colored fruits.
6. Resistant to *Puccinia* rust.

Plants of the new *Hypericum* differ primarily from plants of the female parent selection in the following characteristics:

1. Plants of the new *Hypericum* have smaller leaves than plants of the female parent selection.
2. Plants of the new *Hypericum* have slightly smaller fruits than plants of the female parent selection.
3. Fruits of plants of the new *Hypericum* are pointed in shape whereas fruits of plants of the female parent selection are round in shape.
4. Plants of the new *Hypericum* and the female parent selection differ in fruit color as plants of the female parent selection have light red-colored fruits.
5. Plants of the new *Hypericum* are fully resistant to *Puccinia* rust whereas plants of the female parent selection are slightly resistant to *Puccinia* rust.

Plants of the new *Hypericum* differ from plants of the male parent selection in the following characteristics:

1. Plants of the new *Hypericum* have longer internodes than and are not as bushy as plants of the male parent selection.
2. Fruits of plants of the new *Hypericum* are pointed in shape whereas fruits of plants of the male parent selection are oval in shape.
3. Plants of the new *Hypericum* and the male parent selection differ in fruit color as plants of the male parent selection have light green-colored fruits.

Plants of the new *Hypericum* can be compared to plants of the *Hypericum* 'Kolmred', disclosed in U.S. Plant Pat. No. 13,554. In side-by-side comparisons, conducted in Boskoop, The Netherlands, plants of the new *Hypericum* differed primarily from plants of 'Kolmred' in the following characteristics:

1. Plants of the new *Hypericum* had shorter internodes than plants of 'Kolmred'.
2. Fruits of plants of the new *Hypericum* were pointed in shape whereas fruits of plants of 'Kolmred' were oval in shape.
3. Plants of the new *Hypericum* and 'Kolmred' differed in fruit color as plants of 'Kolmred' had red-colored fruits.
4. Plants of the new *Hypericum* were resistant to *Puccinia* rust whereas plants of 'Kolmred' were susceptible to *Puccinia* rust.

Plants of the new *Hypericum* can also be compared to plants of the *Hypericum* 'Pinky Flair', not patented. In side-by-side comparisons, conducted in Boskoop, The Netherlands, plants of the new *Hypericum* differed primarily from plants of 'Pinky Flair' in the following characteristics:

1. Plants of the new *Hypericum* had shorter internodes than plants of 'Pinky Flair'.
2. Fruits of plants of the new *Hypericum* were pointed in shape whereas fruits of plants of 'Pinky Flair' were rounded in shape.
3. Plants of the new *Hypericum* and 'Pinky Flair' differed in fruit color as plants of 'Pinky Flair' had red-colored fruits.
4. Plants of the new *Hypericum* were resistant to *Puccinia* rust whereas plants of 'Pinky Flair' were susceptible to *Puccinia* rust.

BRIEF DESCRIPTION OF THE PHOTOGRAPHS

The accompanying colored photographs illustrate the overall appearance of the new *Hypericum* plant showing the colors as true as it is reasonably possible to obtain in colored reproductions of this type. Colors in the photographs may differ slightly from the color values cited in the detailed botanical description which accurately describe the actual colors of the new *Hypericum* plant.

The photograph on the first sheet comprises a side perspective view of a typical flowering plant of 'Kolmapuki'.

The photograph on the second sheet is a close-up view of typical flowers of 'Kolmapuki'.

The photograph on the third sheet is a close-up view of a typical plant of 'Kolmapuki' with developed fruits.

DETAILED BOTANICAL DESCRIPTION

Plants used for the aforementioned photographs and following description were grown during the summer in an outdoor nursery in Boskoop, The Netherlands and under cultural practices which closely approximate commercial *Hypericum* production. During the production of the plants, day temperatures ranged from 12° C. to 32° C. and night temperatures ranged from 6° C. to averaged 18° C. Plants were two years old when the photographs and description were taken. In the following description, color references are made to The Royal Horticultural Society Colour Chart, 2007 Edition, except where general terms of ordinary dictionary significance are used.

Botanical classification: *Hypericum×inodorum* 'Kolmapuki'.

Parentage:

*Female, or seed, parent*.—Proprietary selection of *Hypericum×inodorum* identified as code number 261-01, not patented.

*Male, or pollen, parent*.—Proprietary selection of *Hypericum×inodorum* identified as code number 229-04, not patented.

Propagation:

*Type cutting*.—Vegetative cuttings.

*Time to initiate roots*.—About three weeks at temperatures ranging from 18° C. to 30° C.

*Time to produce a rooted young plant*.—About five weeks at temperatures ranging from 18° C. to 30° C.

*Root description*.—Medium in thickness; fibrous; white in color.

*Rooting habit*.—Moderately freely branching; medium density.

Plant description:

*Plant and growth habit*.—Perennial shrub; upright and outwardly spreading plant habit, broad inverted triangle; moderately vigorous growth habit.

*Branching habit*.—Freely basally branching habit with about five main branches each with an average of ten lateral branches; pinching enhances lateral branch development.

*Plant height*.—About 54 cm.

*Plant width (spread)*.—About 46 cm.

*Lateral branch description*.—Length: About 50.5 cm. Diameter: About 6 mm. Internode length: About 4.1 cm. Strength: Moderately strong to strong. Texture: Smooth, glabrous. Color, developing branches: Close to 146D tinged with close to 176C. Color, fully developed branches: Close to 178B.

Foliage description:

*Arrangement*.—Opposite, simple; sessile.

*Length*.—About 5.4 cm.

*Width*.—About 3.4 cm.

*Shape*.—Ovate.

*Apex*.—Obtuse.

*Base*.—Truncate.

*Margin*.—Entire.

*Texture, upper and lower surfaces*.—Smooth to slightly rugose; glabrous.

*Venation pattern*.—Pinnate.

*Color*.—Developing leaves, upper surface: Close to 143A; margins of distal leaves slightly tinged with close to 174A. Developing leaves, lower surface: Between 144A and 146D. Fully expanded leaves, upper surface: Close to N137B; venation, close to 144C to 144D. Fully expanded leaves, lower surface: Close to 138B; venation, close to 145B.

Flower description:

*Flower arrangement and shape*.—Single rotate flowers arranged in terminal and axillary compound cymes; freely flowering habit with about eight flowers per cyme; flowers face mostly upright to outwardly.

*Fragrance*.—None detected.

*Natural flowering season*.—Plants flower continuously from mid-June to mid-August in The Netherlands.

*Flower longevity*.—Flowers last about two or three days on the plant; flowers not persistent.

*Fruit longevity*.—About one month.

*Flower buds*.—Length: About 1.3 cm. Diameter: About 1.1 cm. Shape: Broadly elliptic to broadly ovate. Color: Close to 12A, towards the apex, close to 13A.

*Inflorescence size*.—Height: About 3.5 cm. Diameter: About 7.2 cm.

*Flowers*.—Diameter: About 3.2 cm. Depth (height): About 1.9 cm.

*Petals*.—Quantity and arrangement: Five in a single whorl. Length: About 1.7 cm. Width: About 1 cm. Shape: Elliptic; concave. Apex: Acute to bluntly acute. Base: Attenuate. Margin: Entire. Texture, upper and lower surfaces: Smooth, glabrous. Color: When opening, upper surface: Close to 12A. When opening, lower surface: Close to 12B. Fully opened, upper surface: Close to 12A; color becoming closer to 16C with development. Fully opened, lower surface: Close to 11A.

*Sepals*.—Quantity and arrangement: Five in a single whorl. Length: About 8 mm. Width: About 6 mm. Shape: Ovate to broadly ovate. Apex: Rounded. Base: Broadly cuneate. Margin: Entire. Texture, upper and lower surfaces: Smooth, glabrous. Color: When opening, upper surface: Close to 143A tinged with close to 177B. When opening, lower surface: Between 143B and 144A tinged with close to 176A. Fully opened, upper surface: Close to 143A. Fully opened, lower surface: Close to 144A.

*Peduncles*.—Length: About 1.2 cm. Diameter: About 1 mm. Texture: Smooth, glabrous. Strength: Moderately strong. Color: Close to 144B tinged with close to 172B to 172C.

*Pedicels*.—Length: About 9 mm. Diameter: About 1 mm. Texture: Smooth, glabrous. Strength: Moderately strong. Color: Close to 144A tinged with close to 172B to 172C.

*Reproductive organs*.—Stamens: Quantity per flower: About 75. Filament length: About 1.5 mm. Filament color: Close to 12A. Anther shape: Broadly oval. Anther length: About 0.5 mm. Anther color: Close to 13A. Pollen amount: Scarce. Pollen color: Yellowish. Pistils: Quantity per flower: Single pistil with three stigmas. Pistil length: About 5.5 mm. Stigma shape: Club-shaped. Stigma color: Close to 34B to 34C. Style length: About 5 mm. Style color: Close to 154C to 154D. Ovary color: Close to 154D.

*Fruits*.—Length: About 2 cm. Diameter: About 1.3 cm. Shape: Pointed. Texture: Smooth, glabrous. Color: Close to 40C to 40D; stripes, close to 38A to 38C; with development, stripes become closer to 35B.

*Seeds*.—Length: About 0.9 mm. Diameter: About 0.5 mm. Color: Close to 200A.

Disease & pest resistance: Plants of the new *Hypericum* have been noted to be resistant to *Puccinia* rust. Plants of the new *Hypericum* have not been observed to be resistant to pests and other pathogens common to *Hypericum* plants.

Weather & temperature tolerance: Plants of the new *Hypericum* have been observed to tolerate wind, rain and temperatures ranging from about −20° C. to about 40° C.

It is claimed:

1. A new and distinct *Hypericum* plant named 'Kolmapuki' as illustrated and described.

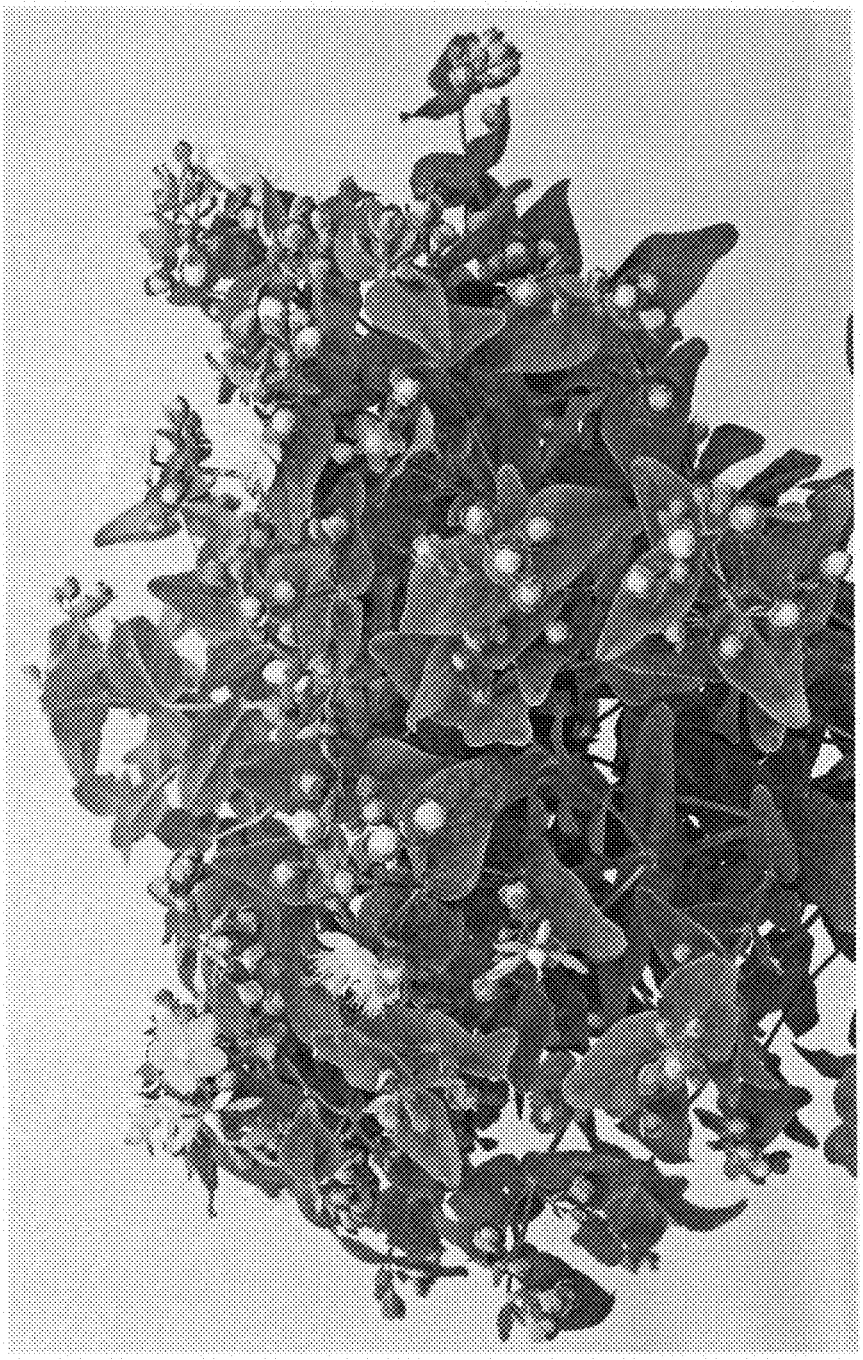

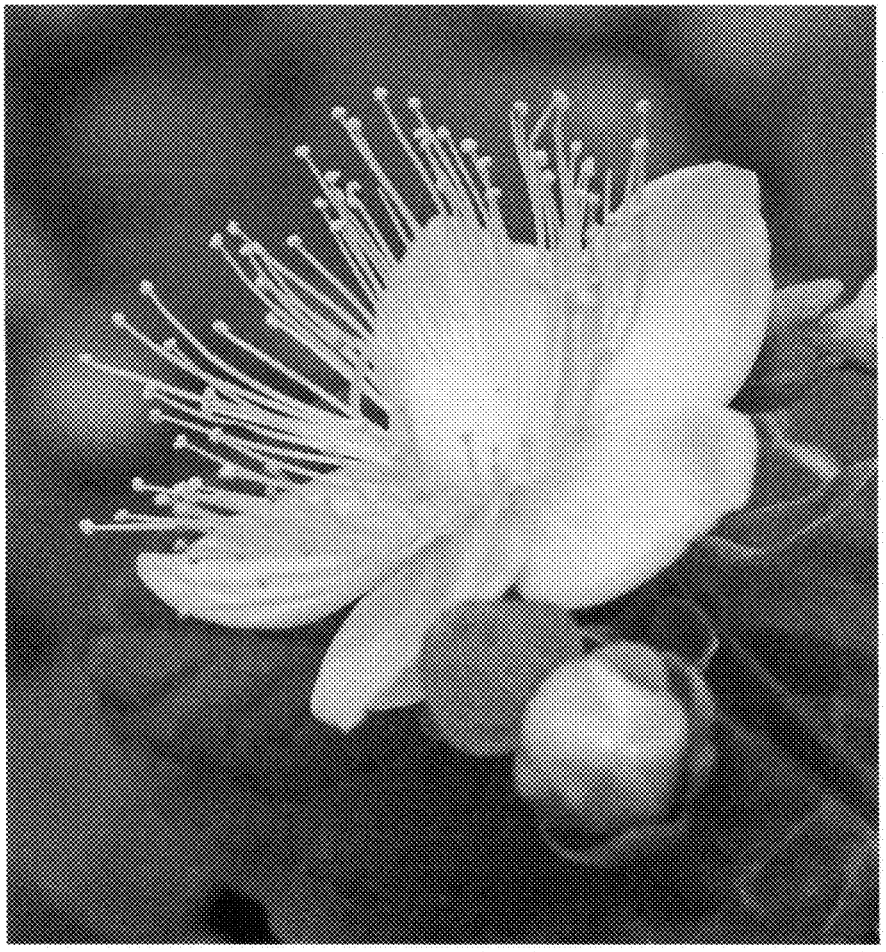

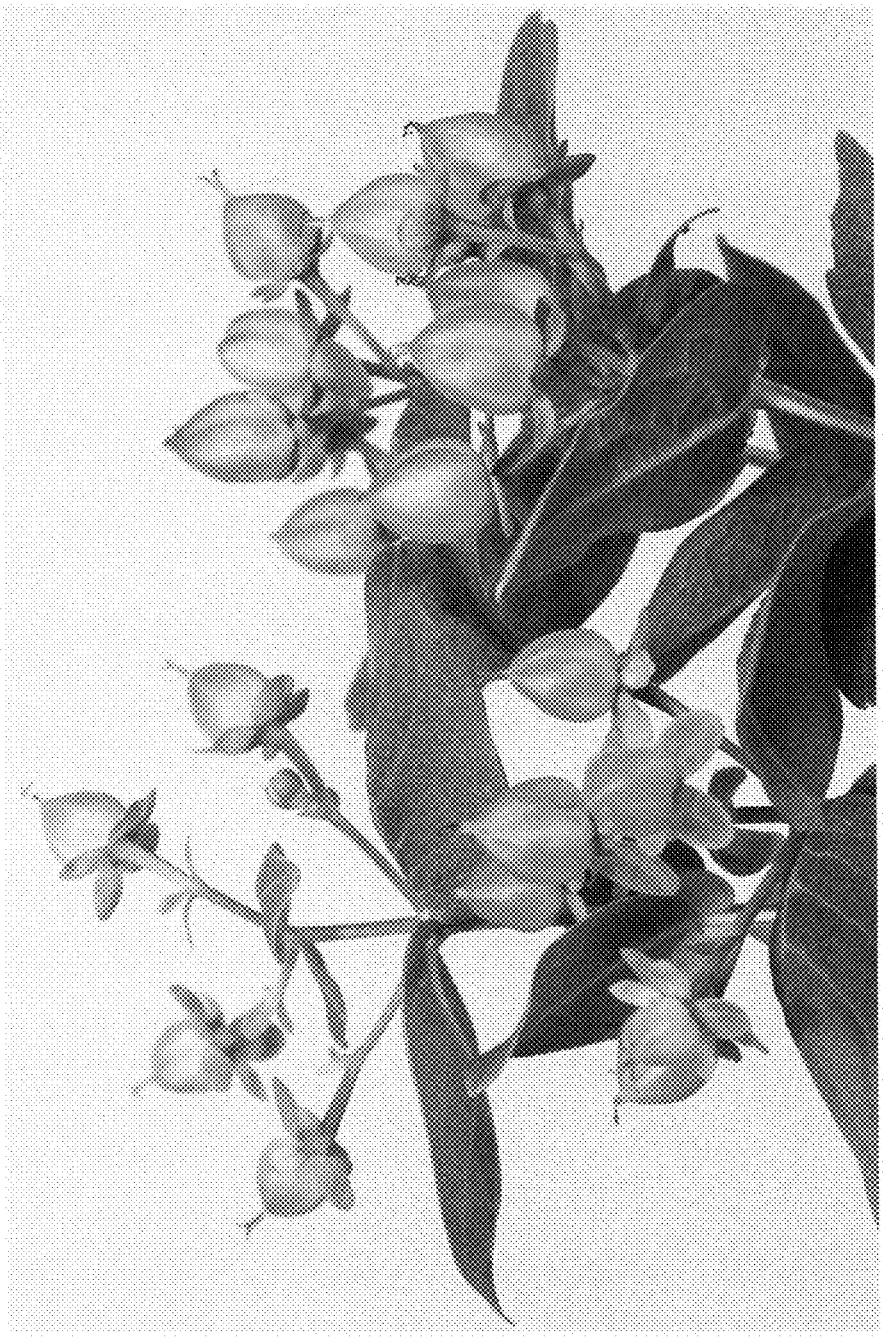

* * * * *